US011272969B2

(12) United States Patent
Hansson

(10) Patent No.: US 11,272,969 B2
(45) Date of Patent: Mar. 15, 2022

(54) OSSEOUS PIN, GUIDE SLEEVE THEREFOR, EXTRACTION MEMBER THEREFOR AND KIT

(71) Applicant: SWEMAC INNOVATION AB, Linköping (SE)

(72) Inventor: Henrik Hansson, Vreta Kloster (SE)

(73) Assignee: SWEMAC INNOVATION AB, Linkoping (SE)

( * ) Notice: Subject to any disclaimer, the term of this patent is extended or adjusted under 35 U.S.C. 154(b) by 102 days.

(21) Appl. No.: 16/342,550

(22) PCT Filed: Oct. 25, 2016

(86) PCT No.: PCT/EP2016/075675
§ 371 (c)(1),
(2) Date: Apr. 17, 2019

(87) PCT Pub. No.: WO2018/077387
PCT Pub. Date: May 3, 2018

(65) Prior Publication Data
US 2019/0239934 A1 Aug. 8, 2019

(51) Int. Cl.
A61B 17/84 (2006.01)
A61B 17/86 (2006.01)
(Continued)

(52) U.S. Cl.
CPC .......... A61B 17/846 (2013.01); A61B 17/863 (2013.01); A61B 17/8883 (2013.01); A61B 17/92 (2013.01); A61B 17/862 (2013.01); A61B 17/8635 (2013.01); A61B 17/8645 (2013.01); A61B 17/8861 (2013.01);
(Continued)

(58) Field of Classification Search
CPC ....... A61B 17/84; A61B 17/846; A61B 17/86; A61B 17/8605; A61B 17/861; A61B 17/8625; A61B 17/863; A61B 17/8635; A61B 17/8645
See application file for complete search history.

(56) References Cited

U.S. PATENT DOCUMENTS 3,675,328 A 7/1972 Weissman
3,842,824 A 10/1974 Neufeld
(Continued)

FOREIGN PATENT DOCUMENTS

CN 200942119 9/2007
DE 10015734 9/2001
WO 0180751 11/2001

Primary Examiner — Anu Ramana
(74) Attorney, Agent, or Firm — Tarolli, Sundheim, Covell & Tummino LLP

(57) ABSTRACT

The present invention relates to an osseous pin (1) for bone fracture fixation. The pin comprises a threaded front section (2) and an unthreaded rear section (3). The threaded front section is configured with two or more kerfs (4) to facilitate breaking of the pin at any one of said kerfs. The present invention also relates to a guide sleeve for use in insertion of the osseous pin (1) into bone fragments at a bone fracture and breaking of said pin at the kerf (4) closest to the entrance site of the pin into the bone fragments. The present invention also relates to an extraction member for use in extraction of the osseous pin (1) from bone fragments at a healed bone fracture and a kit, comprising said components.

11 Claims, 1 Drawing Sheet

(51) Int. Cl.
*A61B 17/88* (2006.01)
*A61B 17/92* (2006.01)
*A61B 90/00* (2016.01)
*A61B 17/90* (2006.01)

(52) U.S. Cl.
CPC ....... *A61B 17/8872* (2013.01); *A61B 17/8891* (2013.01); *A61B 17/90* (2021.08); *A61B 2090/037* (2016.02)

(56) References Cited

U.S. PATENT DOCUMENTS

| | | | | |
|---|---|---|---|---|
| 3,892,232 | A * | 7/1975 | Neufeld | A61B 17/742 606/80 |
| 3,928,915 | A * | 12/1975 | Ellman | A61C 5/35 433/225 |
| 4,053,982 | A * | 10/1977 | Weissman | A61C 5/35 433/225 |
| 6,875,215 | B2 * | 4/2005 | Taras | A61B 17/1637 606/312 |
| 2003/0040751 | A1 | 2/2003 | Weil, Sr. et al. | |
| 2004/0116932 | A1 | 6/2004 | Mazda et al. | |
| 2005/0143734 | A1 | 6/2005 | Cachia et al. | |
| 2008/0124675 | A1 * | 5/2008 | Adams | A61C 8/001 433/174 |
| 2014/0257413 | A1 | 9/2014 | Appenzeller et al. | |
| 2016/0022339 | A1 | 1/2016 | Machida | |

* cited by examiner

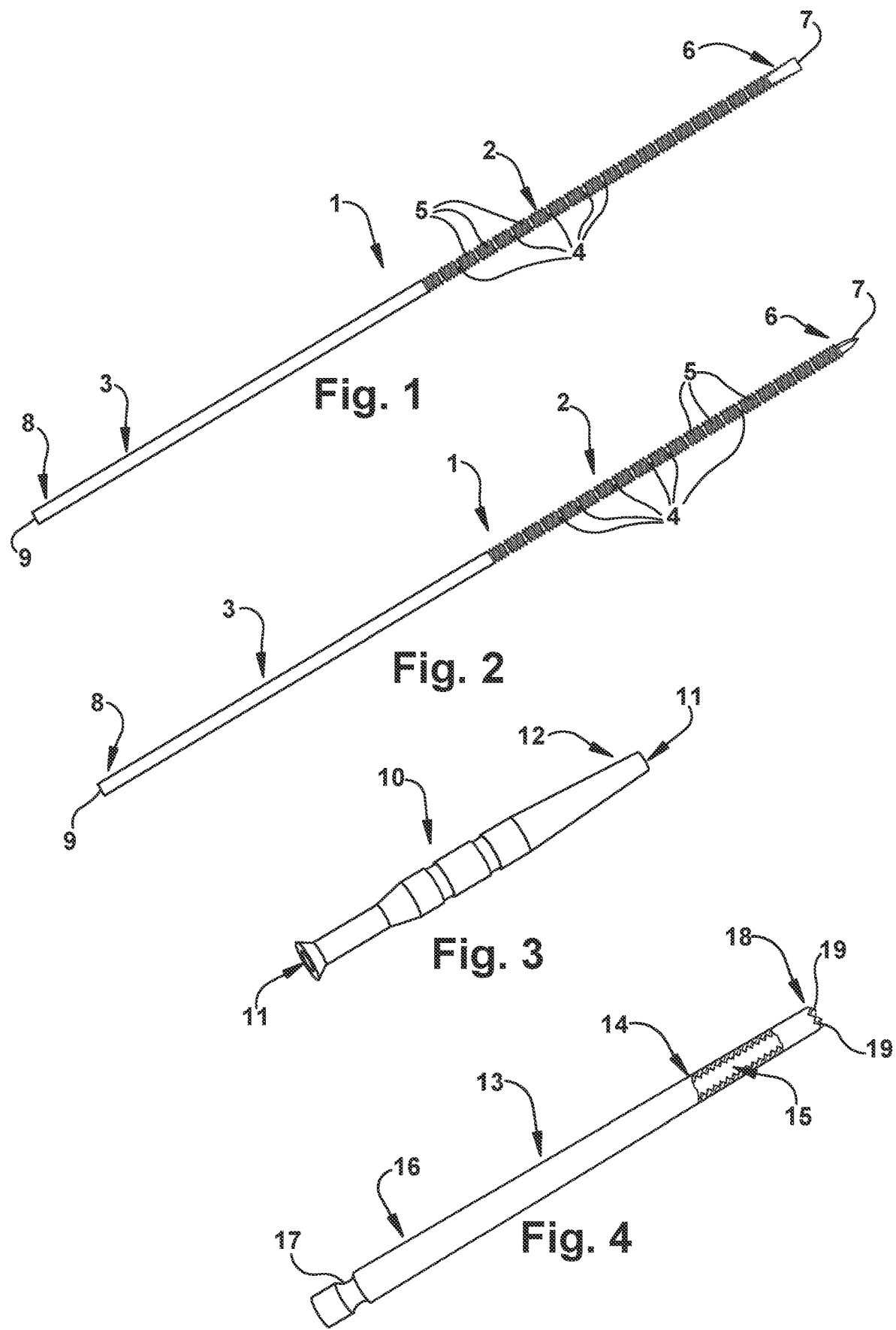

OSSEOUS PIN, GUIDE SLEEVE THEREFOR, EXTRACTION MEMBER THEREFOR AND KIT

RELATED APPLICATION

This application corresponds to PCT/EP2016/075675, filed Oct. 25, 2016, the subject matter, of which is incorporated herein by reference in its entirety.

TECHNICAL FIELD

The present invention relates to an osseous pin for bone fracture fixation.

The present invention also relates to a guide sleeve, configured for use in insertion of the osseous pin into bone fragments at a bone fracture.

Furthermore, the present invention relates to an extraction member, configured for use in extraction of the osseous pin from bone fragments at a healed bone fracture.

Finally, the present invention relates to a kit for bone fracture fixation.

BACKGROUND OF THE INVENTION

Osseous pins of various configurations are already known in the art, cf. e.g. DE 100 15 734 A1, U.S. Pat. Nos. 3,842,824 A, 3,675,328 A, and US 2005/143734 A1.

However, prior art osseous pins are often problematic because they tend to loosen and However, these prior art osseous pins are often problematic because they tend to loosen and move out of their engagement with bone tissue or move further into the bone tissue. Also, most osseous pins are left protruding out of the soft tissue around the bone tissue in order to facilitate removal thereof later. The problem therewith is a high tendency of infection such that healing is prevented or the healing process is counteracted or prolonged.

SUMMARY OF THE INVENTION

The object of the present invention is therefore to overcome or at least ameliorate at least one of the disadvantages of the prior art and provide an osseous pin which is safe and reliable in its engagement with bone tissue and which will cause no infections.

This object is achieved by means of an osseous pin according to claim 1, wherein the pin comprises a threaded front section and an unthreaded rear section, and wherein the threaded front section of the pin is configured with two or more kerfs to facilitate breaking of the pin at any one of said kerfs.

An osseous pin as defined above is easy to apply and by breaking the pin at the kerf closest to the entrance site of the pin into bone fragments at a bone fracture, i.e. substantially in level with the bone tissue at said entrance site, there will be no parts of the pin protruding into soft tissue causing infections therein.

Preferred embodiments of the osseous pin are set forth in the appended dependent claims, in the following description and in the drawings.

The guide sleeve for use in insertion of the osseous pin into bone fragments at a bone fracture, is also configured for breaking of said pin at the kerf closest to the entrance site of the pin into the bone fragments.

The extraction member for use in extraction of the osseous pin from bone fragments at a healed bone fracture, comprises a front section which is configured with a threaded, conically tapering hole for threading said extraction member onto the remains of the threaded front section of the pin at the entrance site of said pin into the bone fragments, and a rear section which is configured with a grip for an extraction tool.

The kit for bone fracture fixation comprises the above-mentioned components, i.e. two or more osseous pins of at least one length and/or at least one diameter, at least one guide sleeve and at least one extraction member.

BRIEF DESCRIPTION OF THE DRAWINGS

The above-mentioned and other characterizing features of the osseous pin according to the invention and the advantages therewith will be further described below by means of non-limiting examples with reference to the accompanying drawings, in which FIG. 1 is a schematic perspective view of a first embodiment of the osseous pin of the invention;

FIG. 2 is a schematic perspective view of a second embodiment of the osseous pin of the invention;

FIG. 3 is a schematic perspective view of a guide sleeve for the osseous pin of FIG. 1; and FIG. 4 is a schematic perspective view of an extraction member for the osseous pin of FIG. 1.

It should be noted that the accompanying drawings are not necessarily drawn to scale and that the dimensions of some features of the present invention may have been exaggerated for the sake of clarity.

DETAILED DESCRIPTION OF PREFERRED EMBODIMENTS

The present invention will now be exemplified by embodiments. It should however be realized that the embodiments are included to explain principles of the invention and not to limit the scope of the invention, defined by the appended claims.

As already mentioned, the present invention relates to an osseous pin 1 for bone fracture fixation. As with prior art osseous pins, the osseous pin 1 according to the present invention is available in many different lengths and diameters. The osseous pin 1 may have a length of e.g. 10-15 cm, preferably about 13 cm as in the illustrated embodiments, and a diameter of e.g. 1-5 mm, preferably a diameter of 1.5, 2 or 3 mm. Irrespective of its length or diameter, the osseous pin 1 comprises a threaded front section 2 and an unthreaded rear section 3. The length of the threaded front section 2 of the osseous pin 1 may constitute about 50% of the total length of the pin, as in the illustrated embodiments, but may alternatively, if appropriate, constitute more than 50% or less than 50% of the total length of the pin.

The threaded front section 2 of the osseous pin 1 is configured with two or more kerfs 4 to facilitate breaking of the pin at any one of said kerfs in order to see to that the pin is broken at the kerf closest to the entrance site of the pin into a bone fragment at a bone fracture such that there will be no parts of the pin protruding into soft tissue at said entrance site. The kerfs 4 may be provided e.g. by configuring the threaded front section 2 of the osseous pin 1 with small interruptions of less diameter of the threading 5 thereof. Thus, while the diameter of the osseous pin 1 at the kerfs 4 may be less than the diameter of the unthreaded rear section 3 of the pin, the diameter of the threading 5 of the threaded front section 2 may be substantially equal to the diameter of said unthreaded rear section. In the illustrated embodiments of the osseous pin 1, kerfs 4 are provided along the entire length of the threaded front section 2 of the pin. The distance between respective two kerfs 4 may be e.g. 1-5 mm, preferably about 3 mm. Alternatively, kerfs 4 may be provided also by configuring the threaded front section 2 of the osseous pin 1 with weakenings of some type of the threading 5 itself, which then may be uninterrupted.

In the embodiments of FIGS. 1 and 2, the threaded front section 2 of the osseous pin 1 is configured with a forward end 6 of different types. In the embodiment of FIG. 1, the forward end 6 of the threaded front section 2 is configured with a quadrilateral cross section. Two of the four sides of the forward end 6 are threaded in order to obtain and maintain optimum fixation of the osseous pin 1 in bone tissue. At the substantially rectangular cross section of the forward end 6 of FIG. 1, the two shorter sides are threaded and preferably tapering towards the point 7. In the embodiment of FIG. 2, the forward end 6 of the threaded front section 2 is configured with a triangular cross section. The three sides of the forward end 6 are here unthreaded. On the other hand, compared to the embodiment of FIG. 1, the forward end 6 of the embodiment of FIG. 2 is shorter.

The unthreaded rear section 3 of the osseous pin 1 may, at the rear end 8 thereof, be configured with a grip 9 for engagement by an insertion tool, e.g. in the form of a handle (not illustrated) for screwing the threaded front section 2 of the pin into bone fragments at a bone fracture.

In use, when the osseous pin 1 is about to be inserted into bone fragments at a bone fracture, insertion will be optimized by using a guide sleeve 10 as illustrated in FIG. 3. The guide sleeve 10 functions as a protection of the soft tissue during the insertion and is also configured for use when breaking the osseous pin 1 at the kerf 4 closest to the entrance site of the pin into the bone fragments. The guide sleeve 10 is in the illustrated embodiment configured in a conventional manner with a through-hole 11 for the osseous pin 1 in the longitudinal direction of the guide sleeve. The guide sleeve 10 is further configured with an outer side which is comfortable to grip and is reinforced at the front end portion 12 thereof which is adapted for engaging the bone tissue at the entrance site for the osseous pin 1 in order to facilitate breaking off of the osseous pin at the appropriate kerf 4. The guide sleeve 10 has in the illustrated embodiment a length of about 60 mm, but the guide sleeve may of course have any other suitable length for its intended use and purpose.

After healing of the bone fracture, the osseous pin 1 need to be extracted from the bone fragments into which the pin has been inserted. An extraction member 13 for use thereby is illustrated in FIG. 4. This extraction member 13 comprises a front section 14 which is configured with a threaded, conically tapering hole 15 for threading said extraction member onto the remains of the threaded front section 2 of the osseous pin 1 at the entrance site of said pin into the bone fragments, and a rear section 16 which is configured with a grip 17 for an extraction tool, i.e. an extraction tool in the form of e.g. a handle (not illustrated) which is connectable to said grip. The length of the extraction member 13 is in the illustrated embodiment about 70 mm, but the extraction member may of course have any other suitable length for its intended use and purpose.

The front section 14 of the extraction member 13 has a forward end 18 which may be configured with teeth 19 which surround the opening into the tapering hole 15 for engaging and gripping into the bone tissue around the entrance site of the osseous pin 1. The teeth 19 may be configured such that they at least to some extent can penetrate into the bone tissue when the extraction member 13 is rotated during threading thereof onto the remains of the threaded front section 2 of the osseous pin 1 at the entrance site in order to thereby provide optimum engagement with said threaded front section for extraction thereof. The extraction member 13 can also do without the teeth 19 and simply have the forward end 18 configured for abutment only against the bone tissue.

The threading in the tapering hole 15 is opposite to the threading 5 of the threaded front section 2 of the osseous pin 1, such that the extraction member 13 is threaded onto the remains of the threaded front section of said pin by rotating the extraction member in the opposite direction as when the pin is inserted by screwing it into the bone fragments. Rotation of the extraction member 13 in said opposite direction is continued until the conicity of the hole 15 prevents further threading and/or the front section 14 of the extraction member engages the bone tissue at the entrance site of the osseous pin 1. Further rotation of the extraction member 13 in the same opposite direction then initiates unscrewing of the remains of the threaded front section 2 of the osseous pin 1 and accordingly, extraction of the pin from the bone fragments.

The extraction tool may be configured for use also when an osseous pin 1 is inserted into bone fragments at a bone fracture, i.e. for use as the above-mentioned insertion tool. The unthreaded rear section 3 of the osseous pin 1 must thereby be configured with a grip fitting with the extraction tool, i.e. preferably a grip similar to the grip 17 of the extraction member 13. Accordingly, the grip 17 of the extraction member 13 and the grip 9 by means of which the osseous pin 1 can be engaged by an insertion tool for screwing said pin into bone fragments at a bone fracture, are preferably of the same type.

For the sake of simplicity, a kit for bone fraction fixation may comprise two or more osseous pins 1 of any of the above-mentioned types and of at least one length and/or at least one diameter, at least one guide sleeve 10 of the above-mentioned type, and at least one extraction member 13 of the above-mentioned type. Thus, the kit may comprise osseous pins 1 of one length and/or one diameter as well as guide sleeves 10 and extraction members 13 fitting thereto and multiple kits with osseous pins of different lengths and/or diameters and fitting guide sleeves and extraction members may be available. Osseous pins 1 of different lengths and/or diameters as well as guide sleeves 10 and extraction members 13 fitting thereto may alternatively be included in one and the same kit.

It is obvious to a skilled person that the osseous pin 1, the guide sleeve 10 for insertion thereof into bone fragments at a bone fracture and the extraction member 13 for extraction of the osseous pin from the bone fragments after healing of the bone fracture can be modified within the scope of the appended claims without departing from the idea and purpose of the present invention. The present invention should not be considered as limited by the embodiments described above nor by the figures illustrating these embodiments. Rather, the full scope of the invention should be determined by the appended claims with reference to the description and to the drawings. Thus, the above-mentioned components may all be made of any plastic or metallic material which fulfils the requirements for a problem-free, safe and reliable use thereof. The osseous pin 1 may be used at many various types of fractures, e.g. hand and foot fractures, wrist fractures, elbow fractures, hip and knee fractures, tibia fractures etc.

The invention claimed is:

1. Osseous pin for bone fracture fixation, wherein the pin comprises a threaded front section and an unthreaded rear section, which threaded front section is configured to be inserted into a bone fragment at a bone fracture through an entrance site of the bone fragment, and wherein the threaded front section of the pin comprises:
    a forward end to be inserted into the bone fragment, the forward end of the threaded front section being configured with either a quadrilateral cross section of which two sides are threaded, or a triangular cross section; and
    two or more kerfs provided along an entire length of the threaded front section of the pin and configured as interruptions of a threading of the threaded front section, which interruptions have a diameter that is lesser than a diameter of the threading, wherein the two or more kerfs are arranged at a distance of 1-5 mm between respective two kerfs, wherein the diameter of the threading of the threaded front section of the pin is substantially equal to the diameter of the unthreaded rear section of the pin, and wherein the kerfs are configured to facilitate breaking of the pin at the entrance site when in use.

2. Osseous pin according to claim 1, wherein the distance between respective two kerfs is about 3 mm.

3. Osseous pin according to claim 1, wherein the diameter of the pin at the kerfs is less than the diameter of the unthreaded rear section of the pin.

4. Osseous pin according to claim 1, wherein the unthreaded rear section of the pin is configured with a grip for an insertion tool.

5. Osseous pin according to claim 1, wherein the length of the threaded front section of the pin is about 50% of the total length of the pin.

6. Osseous pin according to claim 1, wherein the forward end of the threaded front section of the pin is configured with the quadrilateral cross section of which two sides are threaded.

7. Osseous pin according to claim 1, wherein the forward end of the threaded front section of the pin is configured with the triangular cross section.

8. Guide sleeve configured for use in insertion of an osseous pin according to claim 1 into bone fragments at a bone fracture and breaking of said pin at the kerf closest to the entrance site of the pin into the bone fragments.

9. Extraction member, configured for use in extraction of an osseous pin according to claim 1 from bone fragments at a healed bone fracture, wherein the extraction member comprises a front section which is configured with a threaded, conically tapering hole for threading said extraction member onto the remains of the threaded front section of the pin at the entrance site of said pin into the bone fragments, and a rear section which is configured with a grip for an extraction tool.

10. Kit for bone fracture fixation, comprising:
    two or more osseous pins according to claim 1 of at least one length and at least one diameter;
    at least one guide sleeve configured for use in insertion of an osseous pin according to claim 1, into bone fragments at a bone fracture and breaking of said pin at the kerf closest to the entrance site of the pin into the bone fragments; and
    at least one extraction member configured for use in extraction of an osseous pin from bone fragments at a healed bone fracture, wherein the extraction member comprises a front section which is configured with a threaded, conically tapering hole for threading said extraction member onto the remains of the threaded front section of the pin at the entrance site of said pin into the bone fragments, and a rear section which is configured with a grip for an extraction tool.

11. Osseous pin according to claim 1, wherein the kerfs are configured to facilitate breaking of the pin at the entrance site so that the broken pin does not protrude out of the entrance site and into soft tissue around the entrance site.

* * * * *